United States Patent
Hock

Patent Number: 5,688,919
Date of Patent: Nov. 18, 1997

[54] PROCESS FOR THE PURIFICATION OF FACTOR XIII, MONOCLONAL ANTIBODIES AGAINST FACTOR XIIIA, THE PREPARATION AND USE THEREOF

[75] Inventor: Johann Hock, Marburg, Germany

[73] Assignee: Behringwerke Aktiengesellschaft, Marburg, Germany

[21] Appl. No.: 275,656

[22] Filed: Jul. 15, 1994

Related U.S. Application Data

[63] Continuation of Ser. No. 932,507, Aug. 20, 1992, abandoned.

[30] Foreign Application Priority Data

Aug. 22, 1991 [DE] Germany ............... 41 27 841.0

[51] Int. Cl.$^6$ .............. C07K 16/36; C07K 16/00; C07K 17/00; C07K 17/06
[52] U.S. Cl. .............. 530/388.25; 530/388.85; 530/412; 530/413
[58] Field of Search .............. 530/388.25, 388.85, 530/413, 412

[56] References Cited

FOREIGN PATENT DOCUMENTS 0087898  9/1983  European Pat. Off.

OTHER PUBLICATIONS

Roitt et al., Immunology (Second Edition), pp. 8.1–8.12, Gower Medical Publishing, London, (1989).
Ikura et al., Agric. Biol. Chem., 51(2):523, 1987.
Lukacoua et al., FASEBJ., 5(4):A515, 1991.
Church et al., "A simple purification of human factor X using a high affinity monoclonal antibody immunoadsorbant", Chem. Abs. 103:3195y (1985).
Ikematsu et al., "Quantitative determination of blood coagulation factor XIII $a_2b_2$ by Elisa", Chem Abs. 111:53777a (1989).
Lorand et al., "Autoimmune antibody (lgG Kansas) against the fibrin stabilizing factor (factor XIII) system", Chem Abs. 108:110500u (1988).
Tajima et al., "Purification of blood coagulation factor VIII by affinity chromatography using monoclonal antibody", Chem. Abs. 112:135586x (1990).
Takechi et al., "Immunoaffinity chromatography of blood coagulation factor IX", Chem. Abs. 112:154828u (1990).
G. Köhler & C. Milstein, "Continuous cultures of fused cells secreting antibody of predefined specificity", Nature, vol. 256, pp. 495–497, (1975).
James W. Goding, "Antibody Production by Hybridomas", Journal of Immunological Methods, 39 (1980) pp.285–308.
R.A. Gniewek et al., "Monoclonal Antibodies Specific For Human Plasma Factor XIII B Subunit and Their Use in the Purification of Human Plasma Factor XIII By Immunoaffinity Chromatography", Fed. Proc. (1985), 44:1070 No. 3857.
G. Lynch et al., "Monoclonal Antibodies to Factor XIII", Thromb. Haemost., (1985), 54:274, No. 01627.
Goodman, Basic & Clinical Immunology, (Fundenberg et al. Ed.), Lange Medical Publications, California, pp. 32–40 (1976).
Lukacova et al., Biochemistry, vol. 30, pp. 10164–10170 (1991).

*Primary Examiner*—Frank C. Eisenschenk
*Attorney, Agent, or Firm*—Finnegan, Henderson, Farabow, Garrett & Dunner, L.L.P.

[57] ABSTRACT

A process for the purification of factor XIII or XIIIA by immunoaffinity chromatography, monoclonal antibodies against factor XIIIA, the preparation thereof and the use thereof are described.

8 Claims, No Drawings

PROCESS FOR THE PURIFICATION OF FACTOR XIII, MONOCLONAL ANTIBODIES AGAINST FACTOR XIIIA, THE PREPARATION AND USE THEREOF

This application is a continuation of application Ser. No. 07/932,507, filed Aug. 20, 1992, now abandoned.

The invention relates to a process for the purification of factor XIII or XIIIA by immunoaffinity chromatography, to monoclonal antibodies against factor XIIIA, and to the preparation thereof and the use thereof.

Factor XIII is a transglutaminase which stabilizes fibrin, which is formed in the last phase of blood coagulation, by forming covalent linkages between fibrin monomers. Factor XIII is found, inter alia, in blood plasma and in platelets. In plasma it occurs as a complex of A and B subunits which are not linked together covalently. Only the free A subunit is present in platelets. Only the A subunit is necessary for the fibrin-stabilizing action. A deficiency of factor XIIIA (congenital or acquired) results in serious disturbances of coagulation which can be treated by replacement of factor XIIIA.

Several processes are known for purifying factor XIIIA from various starting materials but are associated with certain disadvantages such as inadequate purity of factor XIIIA, many purification steps and low yields.

In the purification of proteins from human tissues or body fluids for therapeutic purposes, a high purity is associated with a low risk of transmission of virus particles. In the purification of recombinant proteins from foreign organisms, very high purity is indispensible due to the potential immunogenicity of contaminating host-cell proteins. Purification of factor XIII by affinity chromatography using monoclonal antibodies is therefore a method which both results in improved virus safety (in the case of purification from human tissues or body fluids) and facilitates the required purity of recombinant products being attained.

Purification by immunoaffinity chromatography has been described for a variety of proteins. However, not every monoclonal antibody is suitable for purifying enzymes or other biologically active molecules by means of immunoaffinity chromatography because the conditions required to dissociate the antigen-antibody complex (for example extreme pH values or high concentrations of chaotropic salts) frequently lead to irreversible destruction of the biological activity of the antigen. Purification of factor XIIIA by immunoaffinity chromatography has also been described (Gniewek, R. A. et al. (1985) Fed. Proc. 44:1070) and entailed antibodies against the B subunit being immobilized on a support and the complex of factor XIIIA and factor XIIIB being adsorbed from plasma. Factor XIIIA was then dissociated from the B subunit and thus eluted from the affinity gel. It is not possible to use this process to purify factor XIIIA from human placenta or from recombinant cells, each of which contain only free factor XIIIA.

An object of the invention is therefore to develop a process for the purification by immunoaffinity chromatography of factor XIII or XIIIA from starting materials such as plasma, placenta or extracts or culture supernatants of recombinant cells which contain the genetic information for the factor XIIIA chain.

Surprisingly, monoclonal antibodies against factor XIIIA which are suitable for purifying factor XIII or XIIIA from the said starting materials have been found.

The invention thus relates to a process for the purification of factor XIII or XIIIA by means of immunoaffinity chromatography, which comprises a solution which contains factor XIII or XIIIA being contacted with a monoclonal antibody against factor XIIIA which is bound to a support material (affinity material), separating the affinity material and liquid from one another, and eluting factor XIII or XIIIA from the affinity material in biologically active form.

Monoclonal antibodies for the purpose of the invention include the immunoreactive fragments, which are known per se to the person skilled in the art, of monoclonal antibodies such as, for example, $F_{(ab')2}$, $F_{(ab)}$ or $F_v$ fragments or antigen-binding single chains of antibody molecules or derivatives thereof.

The monoclonal antibodies against factor XIIIA described in the literature belong to the IgM class (Lynch, G. et al. (1985) Thromb. Haemost. 54:274). IgM antibodies are in general not as suitable as IgG antibodies for immunochemical processes because they often have a lower specificity and affinity.

An object of the invention is therefore also to prepare monoclonal antibodies, preferably of the IgG class, against factor XIIIA.

Monoclonal antibodies against factor XIIIA of the IgG class have been obtained after immunizing mice several times with purified factor XIIIA at intervals of four weeks.

The invention thus also relates to monoclonal antibodies against factor XIIIA, preferably of the IgG class, excepting the IgM class.

Monoclonal antibodies can be prepared by the method of Köhler and Milstein (Nature 256:285–308) or by one of the many variants of their method (for example Goding, J. W. (1980), J.Immunol.Meth. 39:285–308), which are known per se to the person skilled in the art, for example in the following way: Mammals, preferably mice or rats, are immunized by several injections at intervals of 1–8 weeks, preferably 4–6 weeks with a liquid containing factor XIII, preferably an emulsion of purified factor XIIIA in Freund's adjuvant. For the last injection, factor XIIIA is administered in aqueous solution, preferably intraperitoneally or intravenously, 3–5 days before the planned date of fusion. To obtain antibody-producing cells, an immunized animal is sacrificed, a lymphatic organ, preferably the spleen, is removed and the lymphocytes are set free. In order to obtain antibody-producing cells which grow permanently in cell culture, the lymphocytes must be immortalized. This can be carried out in a variety of ways, for example by transformation with Epstein-Barr virus or retroviruses. However, the lymphocytes are preferably fused with myeloma cells. Particularly suitable myeloma cell lines are those which do not secrete immunoglobulins, for example the cell lines SP2/0-Ag14 or X63-Ag8.653. The cells can be fused by incubation with polyethylene glycol (PEG) with a molecular weight of 1000–6000 in 30–60% strength solution, but other processes such as, for example, electrofusion are also suitable. Hybrids of lymphocytes and myeloma cells (hybridomas) are selected and grown by cultivation in a suitable nutrient medium.

The hybridomas are tested for the production of specific antibodies 1–3 weeks after the cell fusion. A large number of test systems which are known per se to the person skilled in the art is available for this. An ELISA test system in which factor XIII is adsorbed onto a solid phase is preferably used. The cell supernatants of the hybridomas are initially contacted with the factor XIII on the solid phase, and subsequently factor XIII-specific antibodies are detected by incubation with an enzyme-labeled antibody against mouse IgG and subsequent addition of a chromogenic substrate for the labeling enzyme. Cells which produce specific antibodies against factor XIIIA are cloned by plating out under microscopic inspection or by the limiting dilution method. Clonal cell lines are grown in vitro for obtaining antibodies. Monoclonal antibodies are obtained from the spent culture medium of the cells. A large number of processes is available for this. An affinity chromatography on immobilized protein A or factor XIIIA is preferably carried out.

The purified monoclonal antibodies are then tested for their suitability for the immunoaffinity chromatography. To do this, the individual monoclonal antibodies are coupled to suitable support materials by processes familiar to the person skilled in the art. Various materials are used as supports in affinity chromatography, for example derivatives of agarose, polyacrylamide or cellulose. The antibodies can be coupled after activation of the support, for example with cyanogen bromide, carbodiimide or by oxidation of adjacent hydroxyl groups with periodate. A large number of other support materials and coupling methods are known to the person skilled in the art. In principle, every customary support material and every coupling method which do not impair or impair only slightly the activity of the coupled antibodies are suitable.

The affinity gels with the various monoclonal antibodies are then tested for their suitability for purifying factor XIIIA. To do this, a factor XIIIA-containing solution is pumped through the affinity gel, and the factor XIII activity in the flow-through is determined. Gels to which the factor XIIIA is adsorbed are tested for the possibility of native elution of factor XIIIA. In a preferred procedure, the binding of factor XIIIA to the immunoaffinity gels takes place in a buffer of low ionic strength, at a pH between 5.5 and 8.5 and at a temperature of 4° C. to 37° C. The buffer preferably contains 0.01–0.05 mol/l tris or phosphate and 0–0.1 mol/l NaCl. The subsequent dissociation of the antigen-antibody complex to obtain purified factor XIIIA frequently requires conditions under which the activity of factor XIIIA is irreversibly destroyed. This is why antibodies which allow dissociation of the antigen-antibody complex with retention of the factor XIII activity are required. It is possible in principle to use various mild eluents, for example certain organic solvents, detergents, aqueous solutions of high ionic strength or combinations of various eluents. Preferably used to elute factor XIIIA are high concentrations of an alkali metal or alkaline earth metal salt for example 0.5–3 mol/l NaCl in a buffer with 0.01–0.05 mol/l tris or phosphate at a pH of 5.5–8.5.

The following examples illustrate the invention.

EXAMPLE 1

Preparation of the Immunizing Antigen (Purified Factor XIIIA)

a) Preparation of an immunoaffinity gel for purifying factor XIIIA

Polyclonal antibodies against factor XIIIA were purified from antiserum against factor XIIIA (Behringwerke) by affinity chromatography. To do this, 10 ml of antiserum were pumped through 50 ml of protein SEPHAROSE® (Pharmacia brand agarose). The gel was washed with 500 ml of 0.14 mol/l Na2HPO4, pH 8.0. Bound antibodies were eluted with 100 ml of 0.1 mol/l glycine, pH 3.0 and adjusted to pH 6.5 with 1 mol/l tris, pH 8.0. The antibodies were dialyzed against 0.1 mol/l trisodium citrate, pH 6.5 (coupling buffer) and coupled to SEPHAROSE®4B activated with cyanogen bromide: 15 g of SEPHAROSE®4B activated with cyanogen bromide were suspended in 1 mmol/l HCl, packed into a chromatography column and washed with 1000 ml of HCl (1 mmol/l). The column was subsequently equilibrated with 50 ml of coupling buffer, and the gel was transferred into a closeable vessel containing 40 ml of the purified antibodies (2 mg/ml in coupling buffer) and shaken at room temperature for two hours. The gel was then returned to the column, washed with 100 ml of coupling buffer, placed in a closeable vessel containing 100 ml of ethanolamine-HCl (1 mol/l, pH 8.0) and shaken at room temperature for two hours. The gel was again transferred into the column and washed alternately with 300 ml each of 0.1 mol/l sodium acetate, 1 mol/l NaCl, pH 4.0 and 0.1 mol/l tris, 1 mol/l NaCl, pH 8.0. The procedure was repeated 5 times. Finally, the gel was equilibrated with 0.01 mol/l Na2HPO4, 0.01 mol/l NaH2PO4, 0.15 mol/l NaCl, pH 7.2 (PBS) and was then ready for use.

b) Purification of factor XIIIA 2500 units of placental factor XIII (RFibrogammin, Behringwerke AG) were dissolved in distilled water and pumped through the immunoaffinity gel. The gel was washed with PBS, and once the absorption at 280 nm was below 0.02 was eluted with 0.2M glycine, pH 2.5. The eluate contained factor XIIIA which appeared as a single band in SDS polyacrylamide gel electrophoresis.

EXAMPLE 2

Preparation of Monoclonal Antibodies against Factor XIIIA a) Immunization of mice Female BALB/c mice were immunized by subcutaneous injection of an emulsion of 50 µg of factor XIIIA (prepared as in Example 1) in complete Freund's adjuvant (day 1). 30 µg of factor XIIIA, emulsified in incomplete Freund's adjuvant, was likewise injected subcutaneously on each of days 28 and 56. This was followed on day 92 by an intraperitoneal injection of 100 µg of factor XIIIA in 0.5 ml of physiological saline.

b) Fusion of lymphocytes with myeloma cells

On day 95, after removal of the spleen, lymphocytes were obtained by mechanical disintegration (about $1 \times 10^8$ cells). The lymphocytes were washed in Dulbecco's modified Eagle's medium (DMEM), mixed with $5 \times 10^7$ cells of the myeloma cell line SP2/0-Ag14 and spun down. The supernatant was completely removed and then 0.5 ml of a 50% strength solution of polyethylene glycol 4000 in DMEM was added dropwise to the cell pellet over the course of one minute. The suspension was incubated at 37° C. for 90 seconds and subsequently diluted by addition of 7.5 ml of DMEM over a period of 5 minutes. After incubation at room temperature for 10 minutes the volume was made up to 40 ml with DMEM, and the cells were spun down. The supernatant was aspirated off and then the cells were resuspended in DMEM containing 20% fetal calf serum (FCS) and 13.6 mg/ml hypoxanthine, 0.18 mg/ml aminopterin, 3.9 mg/ml thymidine (HAT medium) and inoculated on 6 microtiter plates (200 µl per well). Used medium was replaced by fresh at intervals of 3–4 days, and HAT medium was replaced by HT medium after 10 days.

c) Assay for antibodies against factor XIIIA 14 days after the fusion, the cell culture supernatants of the fused cells were assayed for antibodies against factor XIIIA by an enzyme immunoassay: polystyrene microtiter plates were incubated with 0.5 µg/ml factor XIIIA in 0.1 mol/l NaCl, 0.1 mol/l sodium acetate, pH 5.5 (4° C., 24 h). Subsequently cell culture supernatants were applied (37° C., 2 h), followed by incubation with a peroxidase-conjugated antibody against mouse IgG. The substrate used was a solution of 0.1% (weight/volume) 2,2'-azino-bis(3-ethylbenzothiazoline-6-sulfonic acid) and 0.012% (volume/volume) H2O2 in 0.1 mol/l citric acid, 0.1 mol/l Na2HPO4, pH 4.5. After incubation at 37° C. for 30 min, the absorption at 405 nm was measured. Between the individual incubation steps the wells of the assay plates were washed with PBS/Tween.

d) Cloning of antibody-producing cell lines

Cells whose supernatants showed a strongly positive reaction (absorption>1.5) in the enzyme immunoassay described were cloned by the limiting dilution method. For this, about 60 cells in DMEM containing 20% FCS and 5% RHECS (Costar) were distributed over the 96 wells of a cell culture plate. Individual clones were identified under the microscope and assayed for antibody production. The cloning was repeated twice.

e) Purification of monoclonal antibodies

Clonal cell lines were transferred into roller bottles and cultivated in Iscove's modified Dulbecco's medium to produce antibodies. Cells were removed by centrifugation and filtration through paper filters and the supernatant was concentrated about 10-fold by ultrafiltration. The concentrate was passed through protein SEPHAROSE® CL-4B (Pharmacia brand agarose), and bound IgG was eluted with 0.2 mol/l glycine/HCl, pH 3.0. The protein-containing fractions were dialyzed against 0.1 mol/l citrate, pH 6.5, and concentrated to about 5 mg/ml by ultrafiltration.

EXAMPLE 3

Purification of Native Placental Factor XIIIA by Immunoaffinity Chromatography

Lyophilized concentrates of placental factor XIII FIBROGAMMIN®, Behringwerke AG) were dissolved in distilled water. 10 ml portions of the solution (corresponding to 600 units of factor XIII with a specific activity of 5.2 U/mg) were pumped through an affinity gel with a monoclonal antibody (purified as in Example 2 and coupled as in Example 1 to SEPHAROSE® 4B activated with cyanogen bromide). Subsequently unbound protein was washed off the column with 100 ml of washing buffer (0.03 mol/l NaCl, 0.02 mol/l Na2HPO4, pH 7.4). Factor XIIIA was eluted with washing buffer which contained 1 mol/l NaCl. The specific activity was 90–105 U/mg; the protein appeared as one band with a molecular weight of 75,000 Dalton in SDS polyacrylamide gel electrophoresis.

I claim:

1. A process for the purification of coagulation factor XIII or XIIIA by immunoaffinity chromatography, said process comprising:

a) contacting a solution which contains factor XIII or XIIIA with a monoclonal antibody bound to a support matrix;

b) separating the solution from the support matrix, and;

c) eluting factor XIII or XIIIA from the support matrix in a biologically active form, wherein said monoclonal antibody binds the alpha subunit of factor XIII or XIIIA and wherein said monoclonal antibody is not of the IgM class.

2. The process as claimed in claim 1, wherein an immunoreactive fragment of said monoclonal antibody is bound to the support matrix.

3. The process as claimed in claim 1, wherein said monoclonal antibody of the IgG class is used.

4. The process as claimed in claim 1, wherein a buffer which contains 0.5–3 mol/l of an alkali metal or alkaline earth metal salt is used for elution.

5. A monoclonal antibody which specifically binds to the alpha blood coagulation factor XIIIA, except of the IgM class, wherein said monoclonal antibody enables the elution of factor XIIIA bound to said antibody with retention of the biological activity of said factor XIIIA.

6. A monoclonal antibody as claimed in claim 5 of the IgG class.

7. A monoclonal antibody as claimed in claim 5 bound to a support matrix.

8. A process for purifying factor XIII or XIIIA wherein a monoclonal antibody or antigen binding fragment thereof is used and wherein said monoclonal antibody binds the alpha subunit of factor XIII or XIIIA and said monoclonal antibody is not of the IgM class.

* * * * *

UNITED STATES PATENT AND TRADEMARK OFFICE
CERTIFICATE OF CORRECTION

PATENT NO. : 5,688,919
DATED : November 18, 1997
INVENTOR(S) : Johann HOCK

It is certified that error appears in the above-indentified patent and that said Letters Patent is hereby corrected as shown below:

Claim 5, column 6, line 26, after "alpha", insert --subunit of--.

Signed and Sealed this

Ninth Day of June, 1998

Attest:

BRUCE LEHMAN

Attesting Officer

Commissioner of Patents and Trademarks